(12) United States Patent
Jimenez

(10) Patent No.: US 6,893,427 B1
(45) Date of Patent: May 17, 2005

(54) CATHETER WITH THERMORESPONSIVE DISTAL TIP PORTION

(75) Inventor: Oscar Jimenez, Coral Gables, FL (US)

(73) Assignee: Vascon, LLC, Miami, FL (US)

( * ) Notice: Subject to any disclaimer, the term of this patent is extended or adjusted under 35 U.S.C. 154(b) by 0 days.

(21) Appl. No.: 09/533,493

(22) Filed: Mar. 23, 2000

(51) Int. Cl.⁷ .............................................. A61M 25/00
(52) U.S. Cl. ........................ 604/525; 604/527; 604/531
(58) Field of Search ................. 604/529, 527, 604/631, 264, 523, 525, 530, 531, 532, 103.1

(56) References Cited

U.S. PATENT DOCUMENTS

| | | | | |
|---|---|---|---|---|
| 5,163,431 A | * | 11/1992 | Griep | 600/435 |
| 5,370,109 A | * | 12/1994 | Cuny | 600/151 |
| 5,423,771 A | * | 6/1995 | Imran | 604/531 |
| 5,423,773 A | * | 6/1995 | Jimenez | 604/526 |
| 5,445,140 A | * | 8/1995 | Tovey | 600/117 |
| 5,445,624 A | * | 8/1995 | Jimenez | 604/525 |
| 5,725,513 A | | 3/1998 | Ju et al. | 604/280 |
| 5,762,630 A | * | 6/1998 | Bley et al. | 600/585 |
| 5,776,114 A | * | 7/1998 | Frantzen et al. | 600/143 |
| 5,811,043 A | | 9/1998 | Horrigan et al. | |
| 5,944,701 A | * | 8/1999 | Dubrul | 600/585 |
| 5,957,966 A | * | 9/1999 | Schroeppel et al. | 607/119 |
| 5,997,526 A | | 12/1999 | Giba et al. | |
| 6,001,078 A | | 12/1999 | Reekers | |
| 6,002,969 A | | 12/1999 | Machek et al. | |
| 6,024,764 A | | 2/2000 | Schroeppel | |
| 6,102,933 A | | 8/2000 | Lee et al. | 606/209 |
| 6,149,996 A | * | 11/2000 | Helgerson et al. | 604/525 |
| 6,159,187 A | * | 12/2000 | Park et al. | 604/264 |
| 6,245,053 B1 | * | 6/2001 | Benjamin | 264/345 |
| 6,325,790 B1 | * | 12/2001 | Trotta | 604/523 |

FOREIGN PATENT DOCUMENTS

| | | |
|---|---|---|
| EP | 0 334 509 | 9/1989 |
| EP | 0 448 886 | 10/1991 |
| EP | 0 856 330 | 8/1998 |

OTHER PUBLICATIONS

Ex parte Parks, 30 USPQ 2d 1234 (1993).*
Ex parte Grasselli, 231 USPQ 393 (1983).*
www.puchina.com/chinese/yemian/ky-yanfa/jishu/jw-ziliaoku/js-0004.htm.*
Abstracts issue 8: http://www.askpera.com/imperative/Issue8/PDFs/Issue%208%202003.pdf "Memorable Plastics Shape up for New Uses".*
http://www.manufacturing.net/dn/index.asp?layout=article&articleid=CA151359 "Exotic materials enter the marketplace".*

* cited by examiner

*Primary Examiner*—Michael J. Hayes
(74) *Attorney, Agent, or Firm*—Thomas R. Vigil; Welsh & Katz, Ltd.

(57) ABSTRACT

The catheter assembly comprises a tubular body having a proximal end and a distal end and a thermoresponsive distal tip portion fixed to the distal end of the catheter.

7 Claims, 1 Drawing Sheet

CATHETER WITH THERMORESPONSIVE DISTAL TIP PORTION

BACKGROUND OF THE INVENTION

1. Field of the Invention

The present invention relates to an improved thermoresponsive, soft/hard, distal tip portion for any catheter that provides atraumatic contact with the lumen of a conduit. The distal tip portion is an improvement for many types of catheters used for both, the delivery and withdrawal of fluids and devices, especially by the trans-brachial approach. The applications include interventional guiding catheters, coronary catheters, drainage catheters, chemotherapy delivery catheters, and neuroradiology catheters, among others. The thermoresponsive distal tip portion can be used as a sheath tip for a sheath introducer for peds. Also, it can be used as a sheath tip for a trans-brachial or neuro procedure.

2. Description of the Prior Art

Catheters are thin flexible tubes, which are introduced into a vein or artery and guided to selected sites in the vascular system. Angiographic catheters are employed to inject contrast media into a vessel to visualize the shape, state, topography, functionality and other characteristics of the vessel for the purpose of diagnosing anatomic abnormalities of an organ and its conduits. Such catheters are used, for instance, to diagnose diseases of the heart and the circulatory system.

The guidance of a catheter within a tortuous vessel structure, such as a coronary artery and the arteries supplying the brain, often present difficult challenges. Efficient guidance of the distal portion of the catheter may be achieved by various means, including the use of a guidewire, essentially a long, slim and flexible wire or coil on which the catheter's lumen rides or slides to the desired location. An adjunct to the guidewire, various pre-shaped distal configurations have been widely used for such applications as entry into the coronary arteries from the aorta, or for entering the Circle of Willis within the brain. The thermoresponsive distal tip portion for a catheter of the present invention is directed toward improving the performance of both guidewires and catheters with pre-shaped distal portions. For example, the soft tip minimizes thrombus formation when scraping or damaging sensitive arterial walls during movement of the catheter within a blood vessel.

The introduction of a catheter into a vessel and its maneuvering within a vessel are less traumatic when the distal or leading portion of the catheter is soft at the time the catheter comes in contact with the vessel. A soft distal portion of the catheter made of a polymeric or rubbery material in the range of about 35–40 Shore D hardness is desirable. Nevertheless, the degree of softness may present a problem while the catheter's soft distal tip portion is passed or forced through a percutaneous introducer system including an introducer catheter having a hemostasis valve. The introducer facilitates the percutaneous insertion of the catheter by eliminating the need for a surgical cut-down to the vessel, and the hemostasis valve usually employs a membrane for the catheter to pass through without permitting blood to exit out of the vessel and from the body. When the distal portion is soft and rubbery, it may become severely deformed by the force needed for its insertion through the homeostasis valve. When the soft polymeric or rubbery distal portion demands a great deal of force to be passed through the introducer and hemostasis valve, the soft portion may be damaged, torn or even separated from the rest of the catheter. The excessive traction force or friction is the consequence of the soft rubbery interface with the percutaneous introducer housing, hemostasis valve and cannula. If the entire soft distal end or even a part of it were to detach due to excessive traction, then this may cause serious medical complications, even surgical intervention may become necessary during the catheterization procedure.

A variety of catheter and soft distal tip improvements have been made since the first human catheterization was performed by Forssmann in 1929. An example of such improvement is taught by the Horrigan et al. in U.S. Pat. No. 5,811,043 as well as others. Nevertheless, the prior art of soft distal ends or tips takes into consideration a virtual steady state softness of the distal end within a temperature range of 15 to 40° C. In effect, the soft distal tip portion of the catheter remains soft at both room temperature and body temperature. Certain materials employed for the distal tip portion become even softer at body temperature than at room temperature and lose strength as they become softer. This characteristic may pose a further problem upon completing the catheterization procedure and retrieving the catheter from the body through the percutaneous introducer system, as part of it may tear off and remain inside the vessel.

Other U.S. Patents of interest with respect to thermoresponsive materials are listed below:

| U.S. Pat. No. | Patentee |
|---|---|
| 5,957,966 | Schroeppel |
| 5,997,526 | Giba et al. |
| 6,001,078 | Reekers |
| 6,002,969 | Machek et al. |

SUMMARY OF THE INVENTION

The atraumatic benefits derived by using a catheter with a soft distal tip portion may be offset by the risk of difficulties with the integrity of that portion during catheter introduction and retrieval through a percutaneous introducer system. It is therefore desirable to have a catheter distal terminal whose hardness is approximately equal to the hardness of the catheter body (about 72 Shore D hardness) at room temperature, to allow safe and fast introduction through a percutaneous introducer system, but that distal portion should become softer (35–40 Shore D hardness) shortly after it enters the vessel in the body where the temperature is about 37° C. This thermoresponsive distal terminal changes its physical properties as a function of temperature without changing the general properties of its material. Thus, the passage of the catheter's distal tip portion through the percutaneous introducer is facilitated without risking its integrity, yet the distal part of the catheter becomes soft after passing through the percutaneous introducer system and as it comes into direct contact with a fluid filled conduit, such as a blood vessel, and touches the interior of the vessel. The thermoresponsive soft distal tip portion may become more lubricious as it softens; hence removal of the catheter through the percutaneous introducer is simplified and more secure.

The thermoresponsive raw material for the construction of the catheter's distal tip portion may be chosen to be REMEMOMER™, which is available from Mitsubishi Polyurethane, Memory Products Division, 57 Commerce Drive, Brookfield, Conn. 06804, or any similar material with a critical transition temperature of about Tc=31° C. This material manifests a controlled hardness reduction from 72 Shore D (hard) to 35 Shore D (soft) at 31°. Below 31° C. temperature the material retains its hardness in the range of 72–75 Shore D. The material becomes and remains soft above 31° C. Mitsubishi MM-3500 polyurethane, sold under the trademark REMEMOMER™, or similar thermoresponsive materials may be used for this application.

Catheters within the body are often positioned under fluoroscopic guidance; hence it is necessary for the distal portion of the catheter to be well defined in the fluoroscopic image. Toward that objective, the thermoresponsive material must contain a radiopaque substance to view it under X-rays. Rememomer™ or other similarly thermoresponsive polymers must be loaded or compounded with a radiopaque medium such as barium sulfate, bismuth subcarbonate or one of a variety of metal powders, to enhance their radiopacity. This is achieved by heating the polymer to its melting point and mixing with it the selected radiopaque medium. The final radiopaque compound is molded to form the soft distal portion of a catheter, using conventional insert molding or welding techniques.

The present invention also allows the use of other polymeric materials, such as harder conventional polyurethane resins to dilute the softening properties of the thermoresponsive material. Hence, a specific softness may be titrated as required for a specific application. The titrated material may serve to relieve the zones of stress concentration typically associated with hard-to-soft transitions along the longitudinal axis of a catheter with a soft distal portion.

DESCRIPTION OF THE PREFERRED EMBODIMENT(S)

Figure 1:
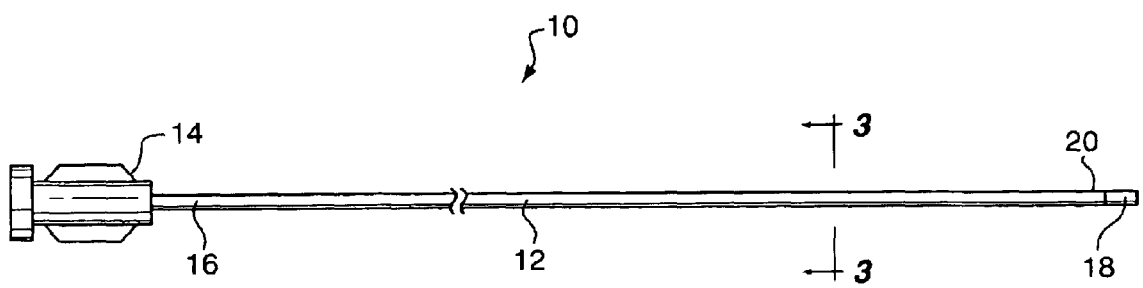
FIG. 1 is a plan view of a catheter constructed according to the teachings of the present invention having a thermoresponsive soft/hard distal tip portion.

Referring to the drawings in greater detail, there is illustrated in FIG. 1 a catheter assembly 10 constructed according to the teachings of the present invention including a catheter 12, a Luer™ connector 14 at a proximal end 16 of the catheter 12 and a thermoresponsive, soft/hard distal tip portion 18 fixed to a distal end 20 of the catheter 12.

Figure 2:
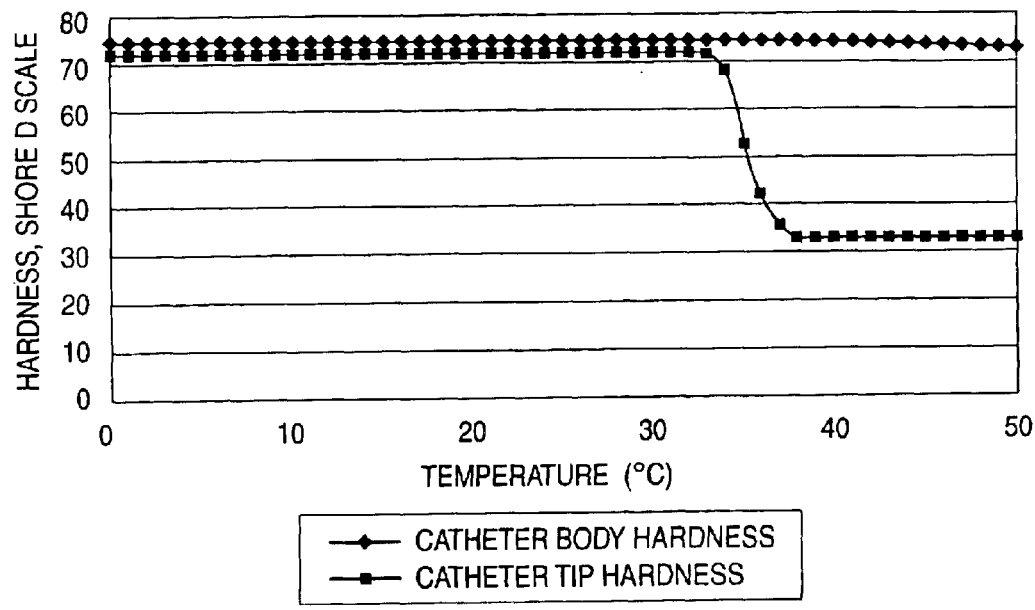
FIG. 2 are graphs of the temperature versus durometer hardness for the catheter and for the distal tip portion.

The hardness of the thermoresponsive material from which the distal tip portion 18 is made is shown as a function of temperature in FIG. 2. The temperature transition region is approximately 5° C. wide.

Figure 3:
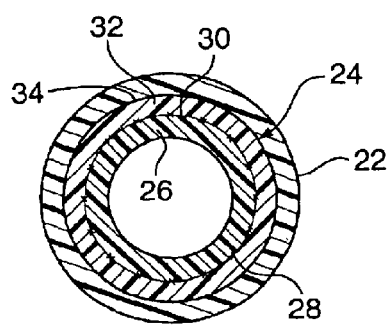
FIG. 3 is a sectional view of the catheter and is taken along line 3—3 of FIG. 1.

Furthermore, the thermoresponsive material may also be used as a jacket 22 to encapsulate a stiffer and harder wire-braided catheter body 24 as shown in FIG. 3. The catheter body 24 includes an inner extrusion 26, a wire braid 28 on the outer surface 30 of the inner extrusion, an outer extrusion 32 and the jacket 22 made of a thermoresponsive material on the outer surface 34 of the outer extrusion 32. This wire-braided construction is often employed to increase the internal pressure limit for a catheter 12 with the goal to increase flow in the catheter 12 without any risk of damage to the catheter structure or the surrounding vessel. The wire-braided structure also improves the torque response of the catheter: when its proximal portion Luer™ connector 14 is rotated by the physician and its distal end portion, distal tip portion 18, follows closely that rotation, despite the tortuosity of the path. The distal tip portion 18 of such a catheter needs to be soft and lubricious to prevent damage to the vessel when the catheter 12 is rotated. In this case the softer material may be extruded and thereby bonded over a harder extrusion or braiding over a relatively long segment of the catheter 12, possibly even the entire length of the catheter may be jacketed in the soft material;

Radiopacity through compounding may be omitted from such a configuration as the wire-braiding does serve as a radiopaque structure.

If additional radiopacity is desired, the thermoresponsive material may be loaded or compounded with a radiopaque medium such as barium sulfate, bismuth subcarbonate or metal powders. The radiopacified thermoresponsive material is used as the jacket 22 to encapsulate the catheter 12 as shown in FIG. 3.

Figure 4:
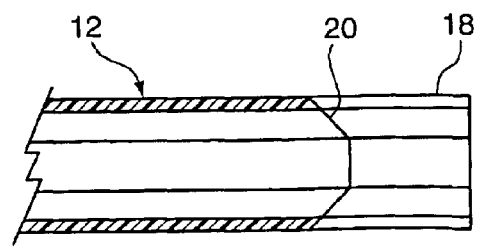
FIG. 4 is a sectional view of the joint between the distal end of the catheter and the distal tip portion and is taken along line 4—4 of FIG. 1.

In this configuration, the thermoresponsive distal tip portion 18 may be welded or insert molded to a tapered end 20 of the catheter 12, as shown in FIG. 4.

The thermoresponsive encapsulation may be accomplished using Mitsubishi RememomerTM MM-3500 polyurethane or any similar thermoresponsive material. Unlike conventional catheters, the thermoresponsive encapsulation hardness is 72–75 Shore D hardness at room temperature and becomes softer to 35 Shore D hardness at 31° C. The soft encapsulation provides an atraumatic, lubricious surface to protect the tissues during catheter manipulation within the vasculature and prevents trauma during characterization. An example of the jacket encapsulation is shown in FIG. 3.

With the catheter assembly 10, the thermoresponsive distal tip portion is inserted through a hemostasis valve of an introducer catheter system and into an introducer catheter until the distal tip portion reaches a blood vessel. Then, further insertion is halted until a short time has passed, e.g., for a few minutes, and possibly up to 5 minutes. This gives the distal tip portion 18 time to heat up and soften. Now the soft distal tip can be inserted into and through the blood vessel to a desired location for performing a medical procedure.

From the foregoing description, it will be understood that the tip distal portion 18 of the present invention has a number of advantages, some of which have been described above and others of which are inherent in the invention. Also, modifications can be made to the tip distal portion 18 and the catheter assembly 10 of the present invention without departing from the teachings of the invention. Accordingly, the scope of the invention is only to be limited as necessitated by the accompanying claims.

I claim:

1. A catheter assembly for use as one of an intravascular catheter, a coronary catheter, a drainage catheter, a chemotherapy delivery catheter or a neuro-procedure catheter and comprising a tubular body having a proximal portion and a distal portion and a separate short distal tip which is coupled to an outer end of said distal portion, said distal portion being made of a temperature responsive hardness memory material comprising radiopague material selected from one of barium sulfate, bismuth subcarbonate or a metal powder compounded with a plastic thermoresponsive material modified or diluted with polyurethane resin to control the softening properties of the thermoresponsive material and said distal portion being harder at temperatures below a critical temperature of approximately 31 degrees C. and softer at temperatures above said critical temperature, said distal tip having a Shore hardness of 72–75 D at temperatures below said critical temperature for facilitating the pushing of said catheter into an introducing catheter and having a Shore hardness of 32–35 D at temperatures above said critical temperature, said distal tip also being made of a thermoresponsive polyurethane material and having a radio-opaque material therein, and said tubular body being coated with a jacket made of said plastic thermoresponsive hardness memory material.

2. The catheter assembly of claim 1 wherein said tubular body is a wire braided body comprising an inner tubular extrusion, a wire braid on the outer surface of said inner tubular extrusion and an outer tubular extrusion extruded over said wire braid.

3. The catheter assembly of claim 1 wherein said distal portion of said tubular body is tapered and said distal tip is welded on or molded on said tapered distal portion.

4. A catheter assembly for use as one of an intravascular catheter, a coronary catheter, a drainage catheter, a chemotherapy delivery catheter or a neuro-procedure catheter and comprising a tubular body having a proximal portion and a distal portion and a separate distal tip which is coupled to an outer end of said distal portion, said distal portion being made of a temperature responsive hardness memory material comprising a radiopague material selected from one of barium sulfate, bismuth subcarbonate or a metal powder compounded with a plastic thermoresponsive material which is modified or diluted with polyurethane resin to control the softening properties of the thermoresponsive material and which is harder at temperatures below a critical temperature of approximately 31 degrees C. and softer at temperatures above said critical temperature, said distal portion having a Shore hardness of 72–75 D at temperatures below said critical temperature for facilitating the pushing of said catheter into an introducing catheter and having a Shore hardness of 32–35 D at temperatures above said critical temperature, said distal tip also being made of a thermoresponsive polyurethane material and having a radio-opaque material therein, and said distal tip being welded on or molded on said distal portion of said tubular body.

5. The catheter assembly of claim 4 wherein said tubular body is coated with a jacket made of said thermoresponsive hardness memory material.

6. The catheter assembly of claim 4 wherein said tubular body is a wire braided body comprising an inner tubular extrusion, a wire braid on the outer surface of said inner tubular extrusion and an outer tubular extrusion extruded over said wire braid.

7. The catheter assembly of claim 4 wherein said distal portion is tapered.

* * * * *